United States Patent
Proksa

(10) Patent No.: US 7,672,423 B2
(45) Date of Patent: Mar. 2, 2010

(54) SHORT SCAN CARDIAC CT ON A QUASI AXIAL TRAJECTORY

(75) Inventor: Roland Proksa, Hamburg (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 12/090,772

(22) PCT Filed: Oct. 11, 2006

(86) PCT No.: PCT/IB2006/053733

§ 371 (c)(1),
(2), (4) Date: Apr. 18, 2008

(87) PCT Pub. No.: WO2007/046036

PCT Pub. Date: Apr. 26, 2007

(65) Prior Publication Data

US 2008/0285708 A1    Nov. 20, 2008

(30) Foreign Application Priority Data

Oct. 20, 2005  (EP) ................................. 05109784

(51) Int. Cl.
*G01N 23/00* (2006.01)
(52) U.S. Cl. .................. 378/11; 378/9; 378/15
(58) Field of Classification Search ............... 378/4–20, 378/92, 114–116
See application file for complete search history.

(56) References Cited

U.S. PATENT DOCUMENTS

| 6,240,157 B1* | 5/2001 | Danielsson ................. 378/15 |
| 6,842,502 B2* | 1/2005 | Jaffray et al. ................ 378/65 |
| 2003/0108146 A1 | 6/2003 | Malamud |
| 2004/0081270 A1 | 4/2004 | Heuscher |
| 2004/0114708 A1 | 6/2004 | Bruder et al. |
| 2005/0100126 A1 | 5/2005 | Mistretta et al. |
| 2005/0111622 A1 | 5/2005 | Bruder et al. |

FOREIGN PATENT DOCUMENTS

| DE | 19953613 A1 | 5/2001 |
| WO | 2004089217 A1 | 10/2004 |
| WO | 2005008716 A1 | 1/2005 |

OTHER PUBLICATIONS

Grass, M., et al.; 3D cone-beam CT reconstruction for circular trajectories; 2000; Phys. Med. Biol.; 45:329-347.
Pack, J. D., et al.; Investigation of saddle trajectories for cardiac CT imaging in cone-beam geometry; 2004; Phys. Med. Biol.; 49:2317-2336.
Parker, D. L.; Optimal short scan convolution reconstruction for fanbeam CT; 1982; Med. Phys.; 9(2)254-257.

* cited by examiner

*Primary Examiner*—Jurie Yun

(57) ABSTRACT

A short scan uses only data from about 180° gantry rotation instead of a full 360° turn. In the provided short scan cardiac CT, a periodical axial focal spot movement is performed during gantry rotation, wherein the acquired data used for image reconstruction results from a 180° rotation of the gantry. After the data acquisition, an approximate reconstruction is performed. In a preferred embodiment the focal spot moves on a short scan saddle trajectory.

17 Claims, 3 Drawing Sheets

SHORT SCAN CARDIAC CT ON A QUASI AXIAL TRAJECTORY

The invention relates to the field of tomographic imaging. In particular, the invention relates to an examination apparatus for examination of an object of interest, to an image processing device, to a method of examination of an object of interest, a computer-readable medium and a program element.

The actual CT detector technology allows for large detectors that are able to cover the entire heart and support axial cardiac imaging. However, the acquired data may not be sufficient for an artefact free reconstruction. This situation becomes even worse if images have to be reconstructed from a so-called short scan.

A short scan uses only data from about 180° gantry rotation instead of full 360° turn. Short scans are very desired for cardiac imaging because of the improved temporal resolution. One way to overcome the pure image quality of axial fan-beam CT is to use a saddle trajectory. This requires a movement of the x-ray focal spot in axial direction during the acquisition. Scanning on a saddle trajectory acquires all data necessary for an exact reconstruction.

However, these methods require a full scan and are not compatible with the short-scan requirement of cardiac CT.

It may be desirable to have an improved reconstruction for short-scan CT.

According to an exemplary embodiment of the present invention, an examination apparatus for examination of an object of interest may be provided, the examination apparatus comprising a radiation source adapted for moving on a scan path around the object of interest and for emitting electromagnetic radiation to the object of interest, a detector unit adapted for detecting image data from the object of interest, and a reconstruction unit adapted for reconstructing the image data on the basis of an approximate reconstruction procedure, wherein the examination apparatus is adapted for performing a periodical movement of a focal spot of the emitted electromagnetic radiation in an axial direction during the movement of the radiation source.

Therefore, according to this exemplary embodiment of the present invention, the data acquisition is performed on the basis of a reciprocating focal spot movement, followed by an approximate image reconstruction. The axial movement of the focal spot may not be synchronised with the scanner rotation.

This may provide for improved image quality even if only a 180° rotation of the gantry is performed.

According to another exemplary embodiment of the present invention, the approximate reconstruction procedure comprises a fan-beam to parallel beam rebinning, a pre-weighting, a one-dimensional filtering, and a three-dimensional back-projection.

Thus, an approximate reconstruction is performed on the basis of a filtered back-projection.

According to another exemplary embodiment of the present invention, the periodical movement of the focal spot is a sinusoidal movement.

According to another exemplary embodiment of the present invention, the focal spot moves on a short scan saddle trajectory resulting from a short scan interval $\lambda_{short}=[\lambda_0, \lambda_0+\pi+\lambda]$, with an arbitrary start angle $\lambda_0$ and a fan angle of $\gamma$.

This interval is, according to another exemplary embodiment of the present invention, related to the gating window of a retrospectively gated cardiac scan.

According to another exemplary embodiment of the present invention, the examination apparatus is adapted as a cardiac CT scanner system.

According to another exemplary embodiment of the present invention, the examination apparatus is adapted as a multi tube CT scanner system comprising a first x-ray tube and a second x-ray tube for increasing an acquisition speed, wherein the first x-ray tube has a first focal spot and the second x-ray tube has a second focal spot, wherein the first focal spot performs a first axial movement on a first trajectory, wherein the second focal spot performs a second axial movement on a second trajectory, and wherein the first trajectory intersects the second trajectory at an intersection point.

By using multiple x-ray tubes the acquisition speed may be significantly increased.

According to another exemplary embodiment of the present invention, the first trajectory of the first focal spot and the second trajectory of the second focal spot are basically the same trajectories. For example, the two trajectories may only differ by a constant, i.e.

$$\vec{a}_1(\lambda) = \vec{a}_2(\lambda+c).$$

According to another exemplary embodiment of the present invention, the one-dimensional filtering is performed on a variety of curved lines.

Furthermore, according to another exemplary embodiment of the present invention, the acquired image data detected by the detector unit results from more than the minimal short scan interval, resulting in a redundancy of the acquired image data, wherein the reconstruction unit is adapted for removing the redundancy.

For example, the acquired image data does not result from a short scan interval $\lambda_{short}=[\lambda_0, \lambda_0+\pi+\gamma]$, but from a larger interval. This may further improve the image quality.

According to another exemplary embodiment of the present invention, the redundancy of the acquired image data is removed on the basis of a Parker weighting, assuring that contributions from all parallel beam projection angles are identical.

This may reduce artefacts from the discontinuities at the projection interval ends.

According to another exemplary embodiment of the present invention, the examination apparatus may be applied as a baggage inspection apparatus, a medical application apparatus, a material testing apparatus or a material science analysis apparatus. A field of application of the invention may be material science analysis, since the defined functionality of the invention may allow for a secure, fast, reliable and highly accurate analysis of material.

According to another exemplary embodiment of the present invention, the examination apparatus may further comprise a collimator arranged between the electromagnetic radiation source and the detector unit, wherein the collimator is adapted for collimating an electromagnetic radiation beam emitted by the electromagnetic radiation source to form a fan-beam.

Furthermore, according to another exemplary embodiment of the present invention, the radiation source may be adapted for emitting a polychromatic radiation beam.

According to another exemplary embodiment of the present invention, an image processing device for examination of an object of interest may be provided, the image processing device comprising a memory for storing image data of the object of interest. Furthermore, the image processing device may comprise a reconstruction unit adapted for reconstructing the image data on the basis of an approximate reconstruction procedure, wherein the examination apparatus is adapted for performing a periodical movement of a focal spot of the emitted electromagnetic radiation in an axial direction during the movement of the radiation source.

Therefore, an image processing device may be provided which is adapted for an improved image reconstruction for short scan CT.

According to another exemplary embodiment of the present invention, a method of examination of an object of interest may be provided, the method comprising the steps of emitting, by a radiation source moving on a scan path around the object of interest, electromagnetic radiation to the object of interest, detecting, by a detector unit, image data of the object of interest, and reconstructing, by a reconstruction unit, the image data on the basis of an approximate reconstruction procedure. During image acquisition a periodical movement of the focal spot of the emitted electromagnetic radiation in an axial direction is performed.

It is believed that this method may provide for improved image reconstruction for short scan cardiac CT.

According to another exemplary embodiment of the present invention, a computer-readable medium may be provided, in which a computer program of examination of an object of interest is stored which, when being executed by a processor, is adapted to carry out the above-mentioned method steps.

Furthermore, the present invention relates to a program element of examination of an object of interest, which may be stored on the computer-readable medium. The program element may be adapted to carry out the steps of emitting electromagnetic radiation to the object of interest, detecting image data of the object of interest, and reconstructing the image data on the basis of an approximate reconstruction procedure, wherein the image data is acquired during a periodical movement of the focal spot in an axial direction.

The program element may preferably be loaded into working memories of a data processor. The data processor may thus be equipped to carry out exemplary embodiments of the methods of the present invention. The computer program may be written in any suitable programming language, such as, for example, C++ and may be stored on a computer-readable medium, such as a CD-ROM. Also, the computer program may be available from a network, such as the WorldWideWeb, from which it may be downloaded into image processing units or processors, or any suitable computers.

It may be seen as the gist of an exemplary embodiment of the present invention that a periodical axial focal spot movement is performed during rotation of the gantry, such that the focal spot moves for example on a short scan saddle trajectory, wherein the acquired data used for image reconstruction results from a (180°+fan-angle)-rotation of the gantry. After data acquisition an approximate reconstruction is performed.

These and other aspects of the present invention will become apparent from and elucidated with reference to the embodiments described hereinafter.

Exemplary embodiments of the present invention will be described in the following, with reference to the following drawings.

The illustration in the drawings is schematically. In different drawings, similar or identical elements are provided with the same reference numerals.

Figure 1:
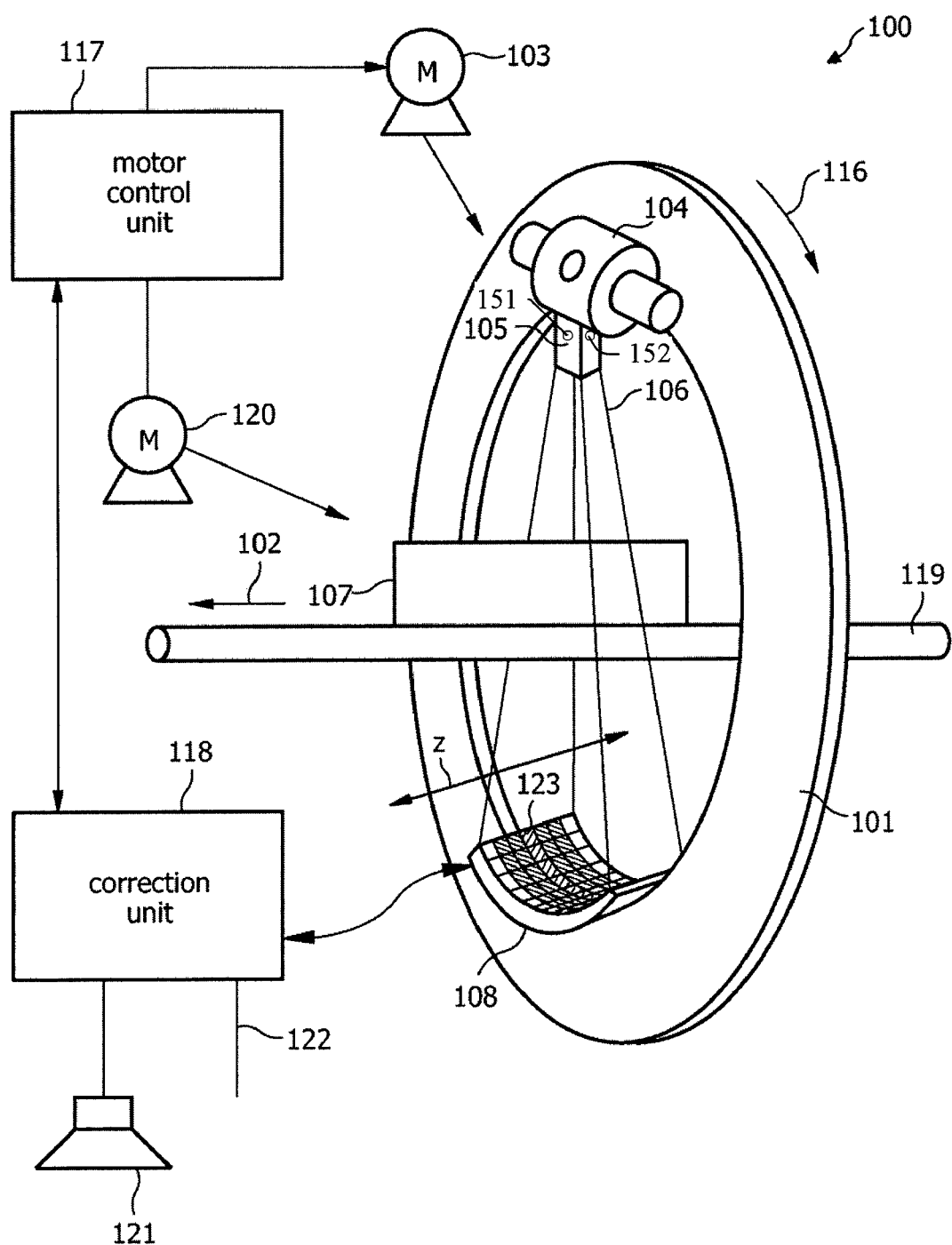
FIG. 1 shows a simplified schematic representation of an examination apparatus according to an exemplary embodiment of the present invention.

FIG. 1 shows an exemplary embodiment of a CT scanner system according to an exemplary embodiment of the present invention. With reference to this exemplary embodiment, the present invention will be described for the application in medical imaging. However, it should be noted that the present invention is not limited to this application, but may also be applied in the field of baggage inspection, or other industrial applications, such as material testing.

The computer tomography apparatus 100 depicted in FIG. 1 is a fan-beam CT scanner. The CT scanner depicted in FIG. 1 comprises a gantry 101, which is rotatable around a rotational axis 102. The gantry 101 is driven by means of a motor 103. Reference numeral 104 designates a source of radiation such as an X-ray source, which, according to an aspect of the present invention, emits a polychromatic radiation.

Reference numeral 105 designates an aperture system which forms the radiation beam emitted from the radiation source to a radiation beam 106. The beam 106 is directed such that it penetrates an object of interest 107 arranged in the centre of the gantry 101, i.e. in an examination region of the CT scanner, and impinges onto the detector 108. As may be taken from FIG. 1, the detector 108 is arranged on the gantry 101 opposite to the source of radiation 104, such that the surface of the detector 108 is covered by the beam 106. The detector 108, which is depicted in FIG. 1, comprises a plurality of detector elements 123 each capable of detecting, in an energy-resolving manner, X-rays or individual photons which have penetrated the object of interest 107.

During a scan of the object of interest 107, the source of radiation 104, the aperture system 105 and the detector 108 are rotated along the gantry 101 in the direction indicated by arrow 116. For rotation of the gantry 101 with the source of radiation 104, the aperture system 105 and the detector 108, the motor 103 is connected to a motor control unit 117, which is connected to a calculation or reconstruction unit 118.

In FIG. 1, the object of interest 107 may be a patient or an item of baggage which is disposed on a conveyor belt 119. During the scan of the object of interest 107, while the gantry 101 rotates around the item of baggage 107, the conveyor belt 119 displaces the object of interest 107 along a direction parallel to the rotational axis 102 of the gantry 101. By this, the object of interest 107 is scanned along a helical scan path. The conveyor belt 119 may also be stopped during the scans to thereby measure single slices. Instead of providing a conveyor belt 119, for example, in medical applications where the object of interest 107 is a patient, a movable table may be used. However, it should be noted that in all of the described cases it may also be possible to perform other scan paths such as the saddle trajectory by moving the table periodically back and forth at twice the frequency of the source-detector arrangement.

The detector 108 may be connected to the reconstruction unit 118. The reconstruction unit 118 may receive the detection result, i.e. the read-outs from the detector elements 123 of the detector 108 and may determine a scanning result on the basis of the read-outs. Furthermore, the reconstruction unit 118 communicates with the motor control unit 117 in order to coordinate the movement of the gantry 101 with motors 103 and 120 with the conveyor belt 119.

The reconstruction unit 118 may be adapted for reconstructing the image data on the basis of a fan-beam to parallel beam rebinning, a pre-weighting, a one-dimensional filtering, and a three-dimensional back-projection, wherein the examination apparatus 100 is adapted for performing a periodical movement of a focal spot of the emitted electromagnetic radiation in an axial direction (e.g. from 151 to 152) during the movement of the radiation source 104, according to an exemplary embodiment of the present invention. A reconstructed image generated by the reconstruction unit 118 may be output to a display (not shown in FIG. 1) via an interface 122.

The reconstruction unit 118 may be realized by a data processor to process read-outs from the detector elements 123 of the detector 108.

Furthermore, as may be taken from FIG. 1, the reconstruction unit 118 may be connected to a loudspeaker 121, for example, to automatically output an alarm in case of the detection of suspicious material in the item of baggage 107.

The computer tomography apparatus 100 comprises the X-ray source 104 adapted to emit X-rays to the object of interest 107. The collimator 105 provided between the electromagnetic radiation source 104 and the detecting elements 123 is adapted to collimate an electromagnetic radiation beam emitted from the electromagnetic radiation source 104 to form a cone-beam. The detecting elements 123 form a multi-slice detector array 108.

Figure 2:
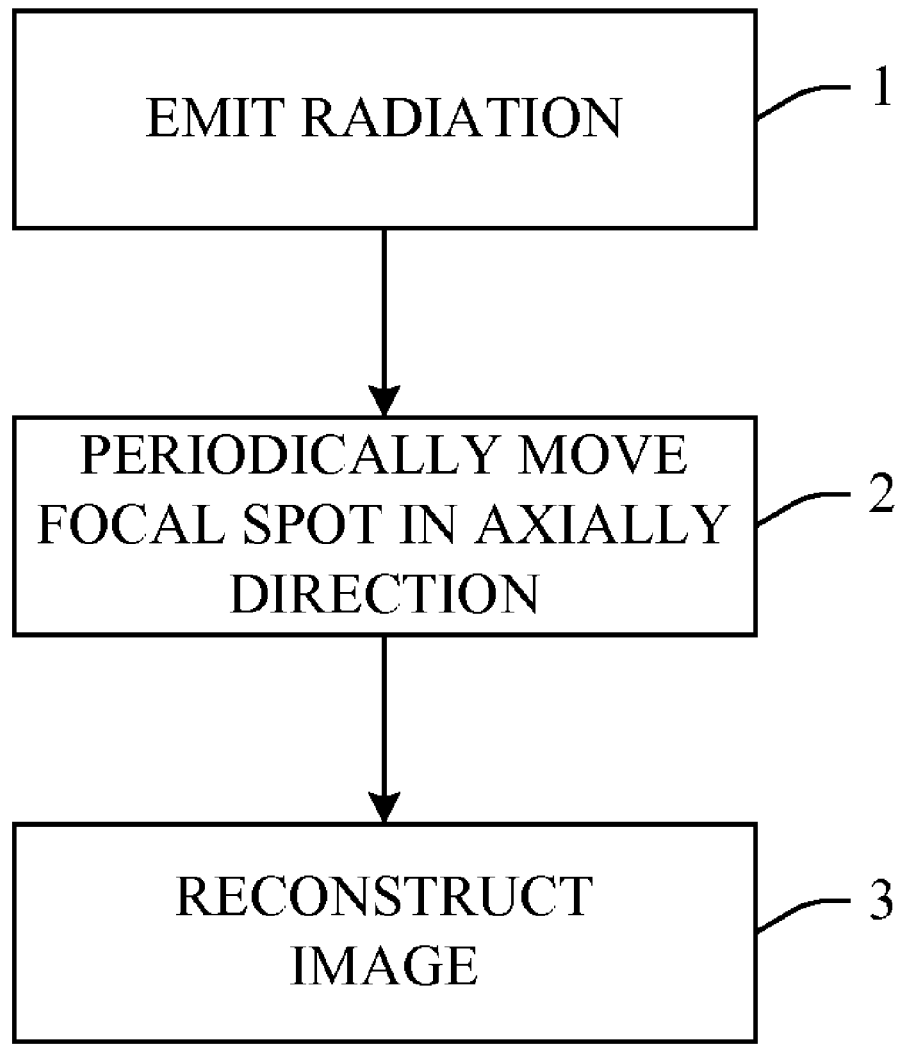
FIG. 2 shows a flow-chart of an exemplary method according to the present invention.
Figure 2:
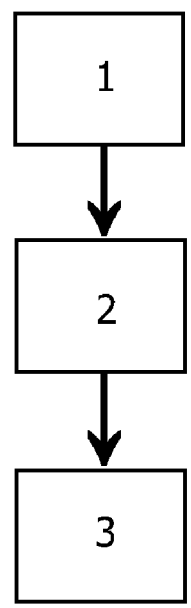

FIG. 2 shows a flow-chart of an exemplary embodiment of a method of examination of an object of interest according to the present invention.

The method starts with step 1 by emitting electromagnetic radiation to the object of interest. This emission of electromagnetic radiation is performed by a radiation source moving on a scan path around the object of interest. The radiation source may be part of a cardiac CT scanner system that supports a periodical movement of the focal spot in axial direction during the gantry rotation.

The periodical movement of the focal spot of the emitted electromagnetic radiation in an axial direction during the movement of the radiation source is performed in step 2.

Such a trajectory may be a sinusoidal movement, for example $$\vec{a}(\lambda) = (R\sin\lambda, R\cos\lambda, D\sin 2\lambda)^T,$$

with a being the trajectory parameterised by $\lambda$, R being the source radius and D being the amplitude of the axial movement. T indicates that the right hand side vector is transposed.

For the following image reconstruction, which is performed in step 3, data from a short scan interval $\lambda_{short} = [\lambda_0, \lambda_0 + \pi + \gamma]$, with an arbitrary start angle $\lambda_0$ and a fan angle of $\gamma$, is used. This interval may be related to the gating window of a retrospectively gated cardiac scan.

The reconstruction consists of:
a fan-beam to parallel beam rebinning,
pre-weighting and one-dimensional filtering, and
a three-dimensional back-projection.

In the following, the reconstruction steps are described in more detail.

Parallel Rebinning

The measured cone beam data g( ) are rebinned to quasi parallel beams:

$$g_P(\theta, u, v) = g(\lambda, \gamma, s),$$

wherein $\theta = \lambda + \gamma$ is a new angular variable, $\gamma$ is the fan angle and s is the axial position of a detector row. The coordinates of the new virtual detector may be as simple as $u = R \sin\gamma$ and $v = s$. However, other mappings may be possible. This mapping may have an impact of the filter step and it may define the effective beam geometry during the back projection.

Pre Weighting $$g_{PW}(\theta, u, v) = g_P(\theta, u, v) \cos(\phi(u, v))$$

with $\phi(u,v)$ being the cone angle.

Filtering $$g_{PWF}(\theta, u, v) = g_{PW}(\theta, u, v) * h(u)$$

with h(u) being a ramp filter or a modified ramp filter.

Back Projection $$f(x) = \pi^{-1} \sum_\theta g_{PWF}(\theta, u_X, v_Y)$$

with $u_X, v_X$ being the detector coordinates of the projection of the object point f(x) onto the projection $g_{PWF}(\ )$.

Several exemplary embodiments of the basic method described above may be performed. For example, the method may be applied to a multi-tube CT system in which multiple x-ray tubes are used to increase the acquisition speed. In such a system all focal spots may perform an axial movement and may either share the same trajectory or have at least intersection points.

Furthermore, the filtering of the data may be performed on a variety of curved lines.

Still further, the method may utilize more than the minimal trajectory interval. The resulting redundancy in the acquired data may be removed with a so-called Parker weighting which may assure that the contribution from all parallel beam projection angles are identical. The Parker weighting is described in Parker, D. L. 1982, Optimal Short Scan Convolution Reconstruction for Fan-beam CT, *Medical Physics* 9(2), 254-257, which is hereby incorporated by reference. This may further reduce artefacts from the discontinuities at the projection interval ends.

Figure 3:
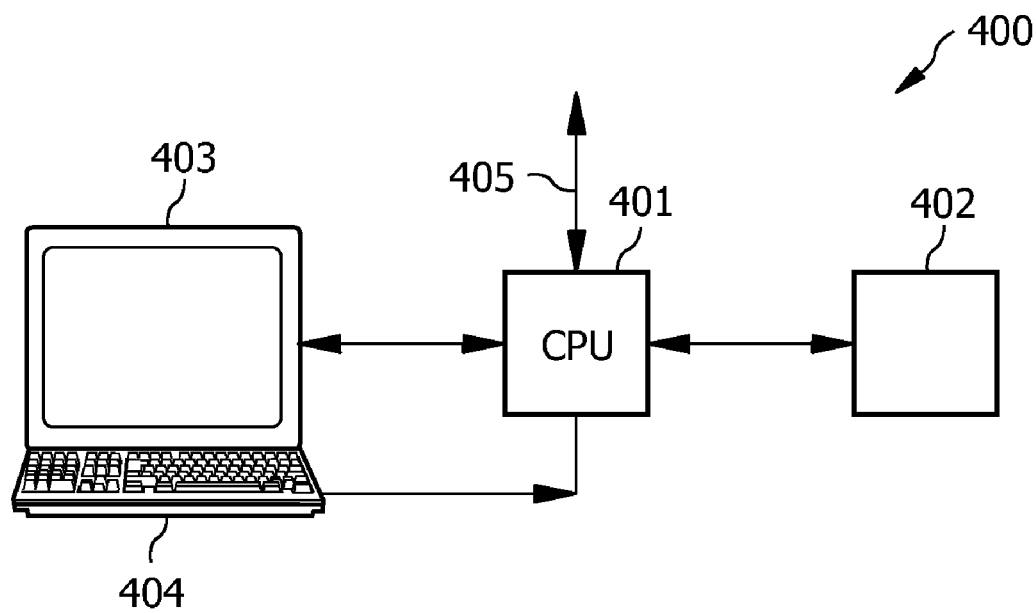
FIG. 3 shows an exemplary embodiment of an image processing device according to the present invention, for executing an exemplary embodiment of a method in accordance with the present invention.

FIG. 3 shows an exemplary embodiment of a processor 401 for executing an exemplary embodiment of the method in accordance with the present invention.

The processing device 400 depicted in FIG. 3 comprises the processor 401 connected to a memory 402 for storing an image depicting an object of interest, such as a heart or other piece of tissue or organ. The data processor 401 may be connected to a plurality of input/output network or diagnosis devices, such as a CT device. The data processor 401 may furthermore be connected to a display device 403, for example, a computer monitor, for displaying information or an image computed or adapted in the data processor 401. An operator or user may interact with the data processor 401 via a keyboard 404 and/or other output devices, which are not depicted in FIG. 3.

Furthermore, via the bus system 405, it may also be possible to connect the image processing and control processor 401 to, for example, a motion monitor, which monitors a motion of the object of interest. In case, for example, a lung of a patient is imaged, the motion sensor may be an exhalation sensor. In case the heart is imaged, the motion sensor may be an electrocardiogram.

Exemplary embodiments of the invention may be sold as a software option to CT scanner console, imaging work stations or PACS work stations.

It should be noted that the term "comprising" does not exclude other elements or steps and the "a" or "an" does not exclude a plurality and that a single processor or system may fulfil the functions of several means of a unit recited in the claims. Also elements described in association with different embodiments may be combined.

It should also be noted, that any reference signs in the claims shall not be construed as limiting the scope of the claims.

The invention claimed is:

1. An examination apparatus for examination of an object of interest, the examination apparatus comprising:
    a radiation source that rotates on a scan path about an axis of rotation around the object of interest and that emits electromagnetic radiation to the object of interest;
    a detector unit that detects image data from the object of interest; and
    a reconstruction unit that reconstructs the image data on the basis of an approximate reconstruction procedure, wherein the approximate reconstruction procedure comprises a fan-beam to parallel beam rebinning, a pre-weighting, a one-dimensional filtering, and a three-dimensional back-projection;
    wherein the examination apparatus performs a periodical movement of a focal spot of the emitted electromagnetic radiation in a direction along the axis of rotation during the movement of the radiation source; and
    wherein the focal spot moves on a short scan saddle trajectory resulting from a short scan interval $\lambda_{short}=[\lambda_0,\lambda_0+\pi+\gamma]$, with an arbitrary start angle $\lambda_0$ and a fan angle of $\gamma$.

2. The examination apparatus of claim 1, wherein a periodical axial movement of the focal spot is a sinusoidal movement.

3. The examination apparatus of claim 1, wherein the short scan interval is related to a gating window of a retrospectively gated cardiac scan.

4. The examination apparatus of claim 1, wherein the examination apparatus is adapted as a cardiac CT scanner system.

5. The examination apparatus of claim 1,
    wherein the radiation source comprises a multi tube CT scanner system comprising a first x-ray tube and a second x-ray tube for increasing an acquisition speed;
    wherein the first x-ray tube has a first focal spot and the second x-ray tube has a second focal spot;
    wherein the first focal spot performs a first axial movement on a first trajectory;
    wherein the second focal spot performs a second axial movement on a second trajectory; and
    wherein the first trajectory intersects the second trajectory at an intersection point.

6. The examination apparatus of claim 5, wherein the first trajectory is basically identical to the second trajectory.

7. The examination apparatus of claim 1, wherein the one-dimensional filtering is performed on a variety of curved lines.

8. The examination apparatus of claim 1,
    wherein the acquired image data results from more than a minimal short scan interval, resulting in a redundancy of the acquired image data; and
    wherein the reconstruction unit removes the redundancy.

9. The examination apparatus of claim 8, wherein the redundancy of the acquired image data is removed on the basis of a Parker weighting, assuring that contributions from all parallel beam projection angles are identical.

10. The examination apparatus of claim 1, configured as one of the group consisting of a baggage inspection apparatus, a medical application apparatus, a material testing apparatus and a material science analysis apparatus.

11. The examination apparatus of claim 1,
    further comprising a collimator arranged between the radiation source and the detector unit;
    wherein the collimator collimates an electromagnetic radiation beam emitted by the radiation source to form a cone-beam.

12. A computer-readable medium, in which a computer program of examination of an object of interest is stored which, when being executed by a processor, is adapted to cause an examination apparatus of claim 1 to carry out the steps of:
    emitting, by the radiation source moving on the scan path around the object of interest, electromagnetic radiation to the object of interest;
    performing a periodical movement of a focal spot of the emitted electromagnetic radiation in an axial direction longitudinally relative to the object of interest during the movement of the radiation source, wherein the focal spot moves on a short scan saddle trajectory resulting from a short scan interval $\lambda_{short}=[\lambda_0,\lambda_0+\pi+\gamma]$, with an arbitrary start angle $\lambda_0$ and a fan angle of $\gamma$;
    detecting, by a detector unit, image data of the object of interest; and
    reconstructing, by a reconstruction unit, the image data on the basis of an approximate reconstruction procedure;
    wherein the approximate reconstruction procedure comprises a fan-beam to parallel beam rebinning, a pre-weighting, a one-dimensional filtering, and a three-dimensional back-projection.

13. An image processing device for examination of an object of interest, the image processing device comprising:
    a memory that stores image data of the object of interest;
    a reconstruction unit that reconstructs the image data on the basis of an approximate reconstruction procedure;
    wherein the approximate reconstruction procedure comprises a fan-beam to parallel beam rebinning, a pre-weighting, a one-dimensional filtering, and a three-dimensional back-projection;
    wherein the image data is based on a periodical movement of a focal spot of emitted electromagnetic radiation in an axial direction during the movement of a radiation source about an axis of rotation around the object of interest, wherein the axial direction is defined by the axis of rotation;
    wherein the image data results from more than a minimal short scan interval, resulting in a redundancy of the acquired image data; and
    wherein the reconstruction unit removes the redundancy.

14. The image processing device of claim 13, wherein the periodical movement of the focal spot is a sinusoidal movement.

15. The image processing device of claim 13, wherein the focal spot moves on a short scan saddle trajectory resulting from a short scan interval $\lambda_{short}=[\lambda_0,\lambda_0+\pi+\gamma]$, with an arbitrary start angle $\lambda_0$ and a fan angle of $\gamma$.

16. A method of examination of an object of interest, method comprising the steps of:
    emitting, by a radiation source moving on a scan path around an axis defined by the object of interest, electromagnetic radiation to the object of interest;
    performing a periodical movement of a focal spot of the emitted electromagnetic radiation in an axial direction during rotation of the radiation source, wherein the axial direction is parallel to the axis of rotation;

detecting, by a detector unit, image data of the object of interest; and reconstructing, by a reconstruction unit, the image data on the basis of an approximate reconstruction procedure;

wherein the approximate reconstruction procedure comprises a fan-beam to parallel beam rebinning, a pre-weighting, a one-dimensional filtering, and a three-dimensional back-projection; and wherein the focal spot moves on a short scan saddle trajectory resulting from a short scan interval.

17. A program element of examination of an object of interest embodied on a computer-readable medium, which, when being executed by a processor, carries out the acts of:

emitting, by a radiation source moving on a scan path around the object of interest, electromagnetic radiation to the object of interest;

performing a periodical movement of a focal spot of the emitted electromagnetic radiation in a direction parallel to an axis of rotation during the movement of the radiation source;

detecting, by a detector unit, image data of the object of interest; and reconstructing, by a reconstruction unit, the image data on the basis of an approximate reconstruction procedure, wherein the approximate reconstruction procedure comprises a fan-beam to parallel beam rebinning, a pre-weighting, a one-dimensional filtering, and a three-dimensional back-projection, wherein the image data results from more than a minimal short scan interval, resulting in a redundancy of the image data; and wherein the reconstruction unit removes the redundancy.

* * * * *